United States Patent [19]

Silver et al.

[11] Patent Number: 5,733,506

[45] Date of Patent: Mar. 31, 1998

[54] GAS SENSORS AND COMPOUNDS SUITABLE THEREFOR

[75] Inventors: Jack Silver, Golders Green; Kenneth Ralph Rickwood, Colchester; Mustafa Tahsin Ahmet, Beckenham, all of England

[73] Assignee: British Technology Group, Ltd., London, England

[21] Appl. No.: 369,319

[22] Filed: Jan. 6, 1995

Related U.S. Application Data

[63] Continuation of Ser. No. 862,542, filed as PCT/GB90/01706 filed Nov. 7, 1990, published as WO91/07658, May 30, 1991, abandoned.

[30] Foreign Application Priority Data

| Nov. 8, 1989 | [GB] | United Kingdom | 8925244 |
| Nov. 8, 1989 | [GB] | United Kingdom | 8925245 |
| Jan. 24, 1990 | [GB] | United Kingdom | 9001636 |

[51] Int. Cl.$^6$ ............ G01N 27/12; G01N 21/78; G01N 31/22
[52] U.S. Cl. ............ 422/90; 422/86; 422/88; 422/98; 436/106; 436/116; 436/138; 73/23.2; 204/415; 204/426
[58] Field of Search ............ 422/82.06–82.09, 422/86, 88, 90, 98, 83, 56; 436/138, 106, 117, 116, 118, 124, 151; 73/23.2, 31.06; 204/415, 426, 598; 540/145, 141, 143, 123; 359/270

[56] References Cited

U.S. PATENT DOCUMENTS

| 4,018,508 | 4/1977 | McDermott et al. | 359/272 X |
| 4,110,015 | 8/1978 | Reddy | 359/270 X |
| 4,139,275 | 2/1979 | Yano et al. | 350/357 |
| 4,306,774 | 12/1981 | Nicholson | 359/270 X |
| 4,330,637 | 5/1982 | Wong | 524/720 |
| 4,350,660 | 9/1982 | Robinson et al. | 422/90 |
| 4,427,267 | 1/1984 | Collins et al. | 350/357 |
| 4,432,612 | 2/1984 | Nicholson et al. | 359/270 X |
| 4,455,378 | 6/1984 | Heiland et al. | 436/126 |
| 4,659,676 | 4/1987 | Rhyne, Jr. | 436/56 |
| 4,718,991 | 1/1988 | Yamazoe et al. | 422/98 X |
| 4,722,905 | 2/1988 | Honeybourne et al. | 436/151 |
| 4,752,447 | 6/1988 | Kimmel et al. | 422/56 |
| 4,775,227 | 10/1988 | Silver | 359/270 X |
| 4,784,477 | 11/1988 | Miyagi et al. | 359/272 X |
| 4,810,655 | 3/1989 | Khalil et al. | 436/138 |
| 4,826,774 | 5/1989 | Nagel | 436/106 |
| 4,832,463 | 5/1989 | Goldner et al. | 359/270 X |
| 4,863,694 | 9/1989 | Kimmel et al. | 422/86 |
| 4,919,891 | 4/1990 | Yafuso et al. | 422/58 |
| 5,045,285 | 9/1991 | Kolesar | 422/98 |
| 5,047,627 | 9/1991 | Yim et al. | 250/227.23 |
| 5,071,770 | 12/1991 | Kolesar | 436/151 |

FOREIGN PATENT DOCUMENTS

| 0 332 935 | 3/1989 | European Pat. Off. . |
| 61-204545 | 3/1985 | Japan . |
| 201140 | 9/1986 | Japan . |
| 204545 | 9/1986 | Japan . |
| 1 602 642 | 11/1981 | United Kingdom . |
| 2 111 987 | 7/1983 | United Kingdom . |
| 2 186087 | 8/1987 | United Kingdom . |

OTHER PUBLICATIONS

N. Ikeda & N. Takahashi. "Neutron activation analysis of the rare earth . . . " Radioisotopes, vol. 27 No. 6, Jun. 1978, pp. 300–305.

(List continued on next page.)

*Primary Examiner*—Harold Y. Pyon
*Attorney, Agent, or Firm*—Nixon & Vanderhye

[57] ABSTRACT

A gas sensor has a gas sensing component which permits measurement of a change in optical absorption and, optionally also a change in electrical conductivity on exposure to an environment containing certain gases. The gas sensing component comprises a metal bis aromatic macrocycle which may be a new mixed rare earth metal bis tetrabenzoporphyrin or tetrabenzoazaporphyrin.

20 Claims, 4 Drawing Sheets

OTHER PUBLICATIONS

Kirk–Othmer's Encyclopedia of Chemical Technology, 3rd Ed., 19. 833, 836, 837.

J. Hak et al. "Kemmlitzite, a new mineral of the Woodhouseire Group,,,", pp. 201–212.

G. Klaus et al. "Schwermineral–aufbereitung . . . " Keramische Zeitschrift 37 (1) 15–17 (1985).

J. Silver. "Chemical chameleons for electronics" New Scientist, 30 Sep. 1989.

R. Jones et al. "Electrical conductivity in langmuir–blodgett . . . " Thin Solid Films 113 (1984), pp. 115–128.

Honeybourne et al "Substituent and Metal–Ion . . . " J. Phys. Chem. Solids, vol. 49, No. 9 (1988) pp. 1003–1008.

Honeybourne et al "Thin Films of Conjugated . . . " Sensors & Actuators, vol. 15, No. 4 (1988), pp. 359–373.

Patent Abstracts of Japan vol. 11, No. 35, 3 Feb. 1987. Abst. #61204545.

Patent Abstracts of Japan vol. 006, No. 179 (14 Sep. 1982), Abst. #57094652.

Pizzarello et al, Kinetics of Color Reversal in Lutetium Diphthalocyanine Oxidation Product Formed with Different Anions, J. Electrochem. Soc. vol. 128, No. 6, Jun. 1981, pp. 1288–1290.

GAS SENSORS AND COMPOUNDS SUITABLE THEREFOR

This is a Rule 62 continuation of application Ser. No. 07/862,542, filed as PCT/GB90/01706 filed Nov. 7, 1990, published as WO91/07658, May 30, 1991, now abandoned.

BACKGROUND OF THE INVENTION

This invention relates to gas sensors and to certain novel compounds which are suitable for use in gas sensors.

The ability of monophthalocyanines, and certain other semi-conducting complex ring systems, to act as gas sensing materials has been known for some years. Thus GB-A-2111987 and GB-A-218607 disclose the use of multi-ring organic semi-conducting compounds in the detection of "NOX" gases. The use of organometallic derivatives of phthalocyanine, tetraarylporphin and dihydrodibenzotetraazaannulene to detect chlorine and NOX gases is also discussed in J. Chem. Soc., Faraday Trans. 1, 80, No. 4, 1984, 851–863, J. Phys. Chem. Solids, 49, No. 9, 1988, 1003–1008 and Sensors and Actuators, 15, No. 4, 1988, 359–370, while FR-A-238440 discloses the use of symmetrical phthalocyanine and porphyrin organometallics in the detection of a range of gases.

Japanese Patent Publications Nos. 57-94652 and 57-93253 disclose the use of europium, lutetium or ytterbium diphthalocyanine complexes adsorbed into a porous and non-transparent support to detect gaseous hydrogen chloride or ammonia by means of a colour change between red and green detected by eye. The methods described in the two Japanese publications rely on exposure of the diphthalocyanine complex to high concentrations of gas in order to produce a detectable effect and are not suitable for use for low concentrations of gas or for detecting the presence of dissolved gases in a liquid medium. Japanese Patent Publication No. 57-108651 concerns the use of a europium diphthalocyanine complex to detect gases in the vapour phase by change in electrical resistance. Overall, the methods described in the Japanese publications do not exhibit sufficient sensitivity to enable one to distinguish between chemically related gases, e.g. different chlorohydrocarbons.

There is therefore a need for development of gas sensors of enhanced sensitivity, capable of distinguishing between gaseous materials and also capable of readily detecting the presence of gases dissolved in solution, even at relatively low concentrations.

SUMMARY OF THE INVENTION

Accordingly, the present invention provides a gas sensor having a gas sensing component supported so as to permit measurement of a change in optical transmission through the component and optionally a change in electrical conductivity on exposure to an environment containing certain gases, which component comprises a metal bis aromatic macrocycle.

The gas sensing component is preferably a metal bisphthalocyanine or a bis macrocycle where each macrocycle is independently a tetrabenzoporphyrin or a mono-, di-, tri- or tetraazatetrabenzoporphyrin. Mixtures of such complexes may be employed. The metal is preferably a rare earth, lead, tin, zirconium, hafnium or a mixture thereof, especially a mixture of rare earths.

Other metals are however also contemplated which are capable of holding the bis macrocycle π-cloud structure together. Preferably the mixture of rare earths is such that at least three rare earths account for at least 10 weight percent each of the total rare earths. Particularly preferred is a mixture of rare earths Known as "heavy fraction". A representative mixture of this type is a mixture containing (based on weight % as the oxide): dysprosium 30%, holmium 10%, erbium 25%, thulium 4%, ytterbium 15%, lutetium 4%, yttrium 5% and others 7%.

The gas detected may be present in a gaseous environment or may be dissolved in a liquid environment. The term 'gas' is used herein to include 'vapour'. Thus the sensor can sense dissolved gas such as chlorine, nitrogen oxides, bromine, $SO_2$ and $H_2S$ in water. The sensor can act as an oxidant/reductant sensor and thus in addition to ions resulting from such dissolved gases, can also detect ions such as perchlorate and dithionite.

The sensor can be of relatively simple construction, for example, the macrocycle component may be used to cover an area of a support which is stationed in or which is capable of being moved into and out of the environment in which it is exposed to the oxidant/reductant. The sensors may be passive or active. Thus passive sensors (such as badges or coated dipsticks) will show a colour change on exposure to a gas or a solution of oxidant or reductant (such as a chlorine-contaminated water reservoir) which change can be monitored by subsequent measurement of optical absorption change. Alternatively, means may be provided to apply a potential difference across the macrocycle component and measure the current required to restore the original colour as a measure of the oxidant/reductant content of the environment. Active sensors may monitor a change in optical transmission and optionally electrical conduction in an on going manner.

It has been found that the sensors of the invention are of sufficient sensitivity to discriminate between gases. Thus the present invention also provides a method of detecting and/or discriminating between gases according to their oxidation potential and/or their electronic structure comprising exposing the gas sensing component of a gas sensor as described above to a gas-containing environment and detecting a change in optical transmission, and also optionally a conductivity change, through the gas sensing component characteristic of the gas. Suitably the change detected is proportional to the concentration of gas.

In certain cases, gases or classes of gases can be actually identified by this method.

The effects detectable optically include both band shifts and also changes in intensity of absorption. In a typical case, a macrocycle as above which normally (i.e. in its ground state) is green will show an absorption shift towards blue on exposure to electron-withdrawing gases such as $NH_3$, $H_2S$, and CO, no change on exposure to nitrogen, and a loss in green intensity and new bands giving a red coloration on exposure to iodine, bromine or chlorine. Gases or vapours such as $CH_2Cl_2$, $CHCl_3$ and $CCl_4$, $C_6H_5Br$ or $C_6H_5Cl$, and others of similar electronic structure, show an absorption shift and a change in intensity of the green band. The material colour reverts on driving off the gas by heating (where possible) or by electrochemical reversal of the effect, i.e. electrochemically.

The gas sensor may be used as originally prepared. However, it has been found advantageous in many cases to apply some form of pretreatment, such as preheating, for example to 140° C., or preconditioning by pre-exposure, for example, to a vapour of a halobenzene. Both pre-heating and pre-exposure may be used. Pre-heating is preferred and has been found to enhance reproducibility significantly in many cases.

Certain of the bis aromatic macrocycles suitable for use in the present invention as gas sensors are new per se. Thus although certain rare earth bisphthalocyanines are known (lutetium, bisphthalocyanines is disclosed as an electrochromic material in EP-A-54587 and europium, lutetium and ytterbium bisphthalocyanines are disclosed in the Japanese references discussed above). However, it has been found that certain new rare earth bis aromatic macrocycles, where at least one of the bridging nitrogen atoms of the phthalocyanine ring system has been replaced by carbon, demonstrate considerable utility as gas sensing materials.

Therefore according to a further aspect of the present invention there is provided a rare earth bis aromatic macrocycle wherein the macrocycles are bis phthalocyanine analogues in which, of the total eight non-coordinating bridging nitrogen atoms of the bis phthalocyanines, at least one has been replaced by carbon. The carbon(s) may be unsubstituted or may bear substituents such as methyl, ethyl, propyl, butyl or higher alkyl, or phenyl, which groups may themselves be substituted. The invention includes mixtures of such bis-macrocyclic compounds.

A mixture of rare earths may be employed. Preferably the mixture of rare earths is a heavy fraction mixture. The novel bis macrocycles, as well as being useful for example for gas sensing, for example detection of $Cl_2$, NO and $NH_3$, are also suitable for use in electrochromic devices in that they exhibit a colour change when a potential difference is applied thereto, in particular a colour change from neutral green to red or from neutral blue to wine red on oxidation, which on reduction moves to indigo.

DETAILED DESCRIPTION OF THE DRAWINGS

The invention will now be described by way of example and with reference to the accompanying drawings in which.

DETAILED DESCRIPTION OF THE INVENTION

Figure 1:
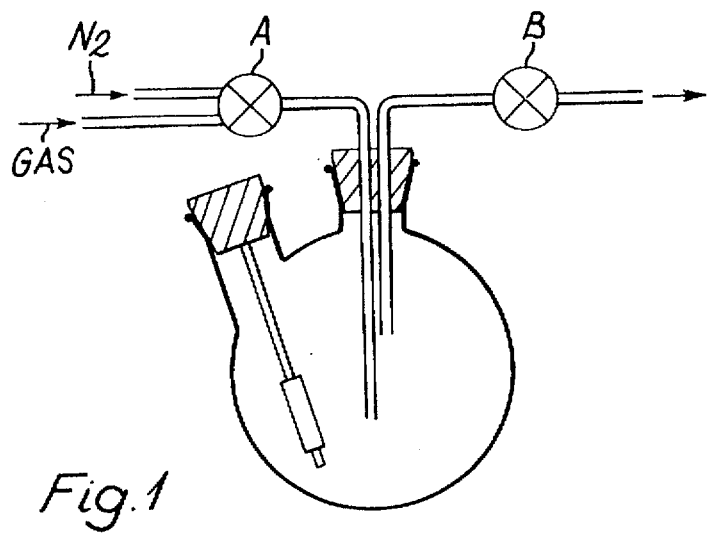
FIG. 1 shows apparatus for sensing gases, suitable when high concentrations are expected.

In FIG. 1, an inlet tap A admits to a transparent vessel either the gas to be investigated, or purging nitrogen. The tap A can also be closed completely. An outlet tap B can be closed (trapping whatever gas is in the vessel) or can be opened to a vacuum pump. In the vessel is mounted a glass slide coated with a bis-macrocycle as described above. The slide can be examined by ultraviolet or visible spectroscopy and has means (not shown) for heating to 140° C. if necessary to drive off any gas and restore it to its original condition.

Figure 2:
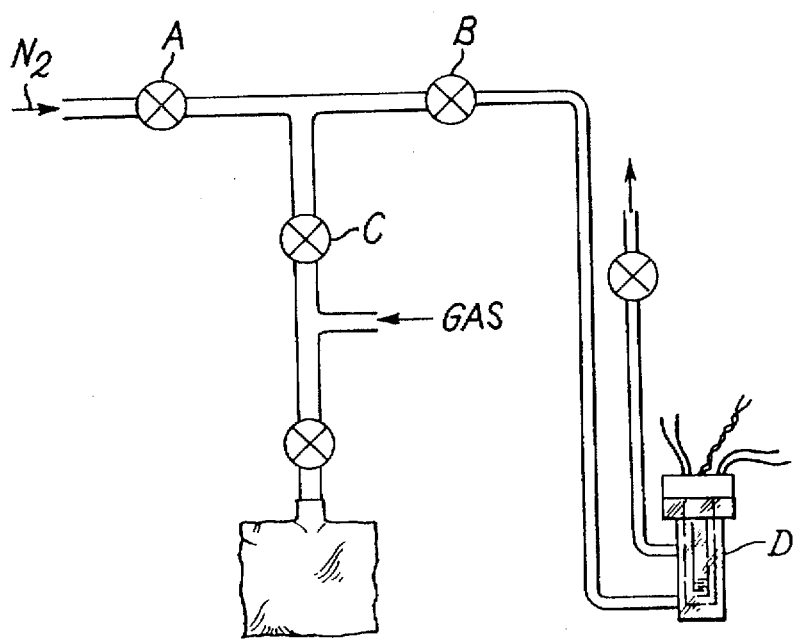
FIG. 2 shows alternative apparatus for sensing gases, suitable when low concentrations are expected.

In FIG. 2, an inlet tap A admits purging or diluting nitrogen to the system, and a tap C downstream thereof admits sample gas, the gas being initially admitted to a collapsible 20-liter bag. A flow regulator B leads to a controlled-temperature conductivity cell (on which optical measurements are also made), which is exhausted through a further flow regulator to a vacuum pump.

Figure 3A:
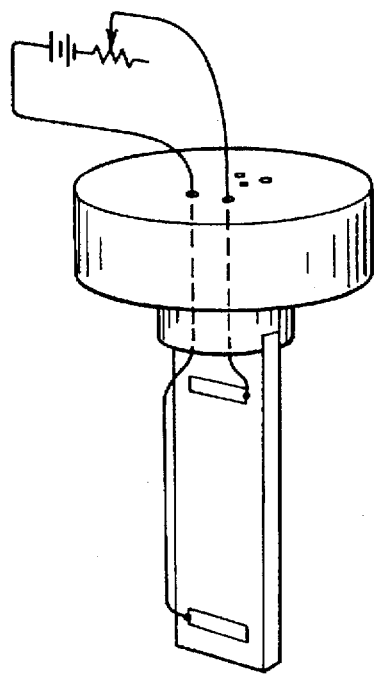
FIGS. 3a and 3b show from different angles an insert for a controlled-temperature conductivity cell which forms part of the apparatus of FIG. 2.

In FIG. 3a, it will be seen that an indium-tin-oxide-coated glass plate has two contact pads, with electric leads, so arranged that the glass can be resistively heated up to 140° C. through the indium-tin-oxide layer.

Figure 3B:
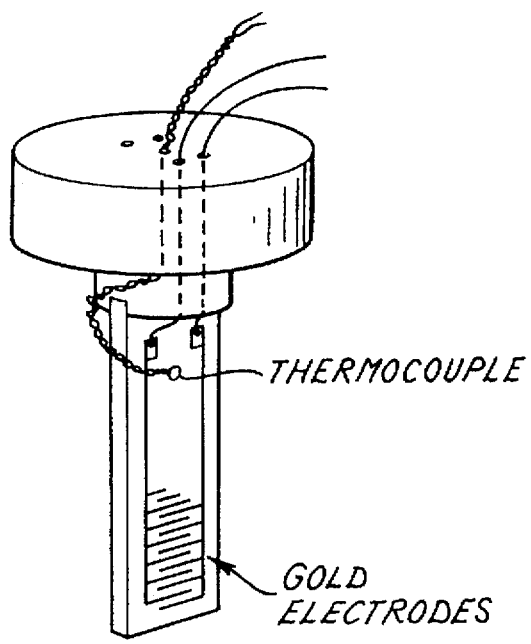

FIG. 3b shows the opposite side of the glass plate of FIG. 3a; two interdigitated gold electrodes, width of all tracks 0.5 mm and gap also 0.5 mm, equivalent length 100 mm, are connected to conductivity apparatus.

Figure 4:
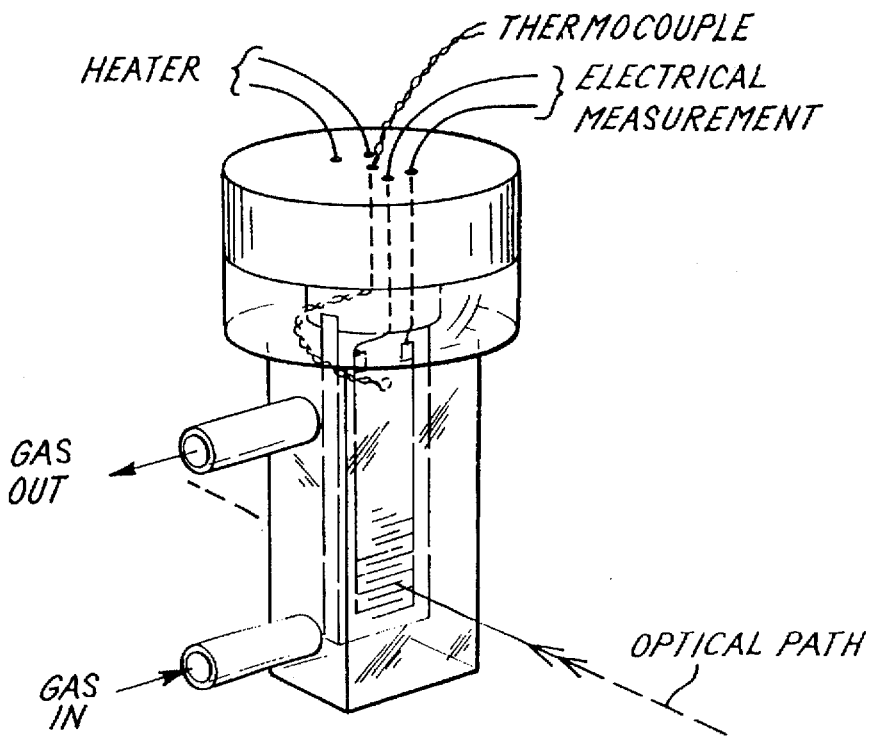
FIG. 4 shows schematically the complete cell whose insert was shown in FIG. 3 and which forms part of the apparatus of FIG. 2.

FIG. 4 shows the complete cell including the plate of FIG. 3. Gas can circulate around the plate, and the whole is transparent, permitting simultaneous optical and electrical measurements.

The plate is coated by sublimation, Langmuir-Blodgett multiple molecular layer deposition, evaporation or any other convenient way with a layer of bis-macrocycle (the material whose optical and electrical properties on exposure to gas are to be monitored—see later).

The relative effects of the different exemplary gases on the sample plates were calculated as follows:

For any specimen gas, the highest light absorbance peak in the visible is measured for the plate before starting, and the highest absorption peak in the visible (this may have shifted to a different wavelength) is measured after 5 seconds' exposure to the gas. Subtract the latter (highest absorbance after exposure) from the former (highest absorbance before exposure) and divide this difference by the former, to ascertain the normalised absorption change.

Before commencing use, the whole system is purged several times with nitrogen and the collapsible bag left empty.

The current required to heat the plate to 130° C. at a flow rate of either one or two liters per minute was determined previously, as were the requisite gas tap settings, and only these two rates were used throughout the study to enable meaningful comparison of results.

Referring now to FIG. 2, while the plate is being heated, tap C is closed and taps A and B are open so nitrogen at a predetermined flow rate passes over the sample. The reasons for passing nitrogen during heating are twofold, firstly it prevents the sample overheating and destroying itself and secondly it ensures that when the gas is drawn from the collapsible bag instead of through tap A there is no change in sample temperature resulting from a difference in flow rate. 10 minutes suffices to reach thermal equilibrium. If the sample is to be at room temperature during the experiment nitrogen is still passed over the sample but obviously the heating stage is missed out.

A known volume of the gas under study is drawn into a gas tight syringe. With taps A and C open the gas being studied is injected at atmospheric pressure from the gas-tight syringe (of capacity 0.02 ml, 0.1 ml, 0.4 ml or 1 ml) through a suitable self-sealing stopper. As the twenty-liter bag fills up with nitrogen the injected gas is mixed and by the time the bag is full it contains a homogeneous mixture of the gas being studied of concentration 1 part per million, 5 ppm, 20 ppm or 50 ppm respectively. This process takes approximately 10 seconds and causes the temperature to rise by a few degrees, but for only a matter of seconds. As soon as the bag is full, tap A is closed and the vacuum pump is turned on. This causes the gas-nitrogen mixture in the bag to be passed through the cell holding the sample (D in FIG. 2) at the preset flow rate.

Both optical (ultraviolet/visible) and electrical conductivity measurements are started prior to the gas-nitrogen mixture being passed over the plate. The UV/Visible spectra are recorded in continual scan mode from 750 to 350 nm which allows one complete spectrum to be taken every 50 seconds, the absorption at peak positions being recorded automatically. It is also possible to take the optical measurements at specific wavelengths (using light-emitting diodes or other specifically designed equipment) in cases where the identity of the gas to be monitored is known in advance. The current measurements are simultaneously noted.

When the bag is empty, tap C is closed and tap A opened to allow nitrogen to pass over the sample. The optical and electrical measurements are recorded continually, the point when the nitrogen was switched on being carefully noted. The measurements are continued until they return to the values prior to admission of the gas. i.e. until the plate recovers. If this does not happen after a reasonable amount of time (about 2 hours), measurements are discontinued and the plate kept hot for several hours after which time measurements are resumed and the amount of recovery is determined.

EXAMPLES

Example 1

Detection of Chlorine by conductivity change.

Conductivity change for varying concentrations of chlorine gas using as gas sensor a sublimed film of heavy-fraction rare earth bis-phthalocyanine are given in Table 1 below.

TABLE 1

| gas concentration current ppm | temperature °C. | Initial current μA | Current after 2 mins μA | rise in conductivity % |
|---|---|---|---|---|
| 50 | 140 | 2.9 | 8.0 | 175 |
| 50 | 150 | 5.0 | 13.0 | 140 |
| 50 | 150 | 4.2 | 15.0 | 280 |
| 5 | 145 | 3.35 | 4.7 | 40 |
| 5* | 155 | 15 | 43 | 186 |
| 50* | 155 | 17 | 58 | 241 |
| 5* | 140 | 12 | 26 | 116 |

*different cell from that of the previous four runs.

Example 2

Detection of Gases by spectroscopic measurement.

The data of Table 2 below were obtained from sensing the gases indicated, using the apparatus of FIGS. 2–4 but without the dilution facility and, as gas sensor, a sublimed film of heavy-fraction rare earth bis-phthalocyanine. The examples have been arranged in order of normalised absorption change as defined previously. However, in other experiments, sensitivity at concentrations of $Cl_2$ down to 5 ppm was observed (especially in conductivity, see Table 1).

A non-preheated plate with the same coating, exposed to hydrogen bromide gas, became almost transparent except for a small band at 705 nm. (On exposure to chlorine, the 705 nm band is much stronger, and there is also a 500 nm band.)

Recovery after heating for 5 h at 140 C was good and gave a spectrum of expected absorbance.

Hydrogen iodide appears to give the same reaction. This shows how the material can discriminate spectrally between HBr, $Cl_2$, $H_2S$ and other gases.

TABLE 2

| Ex No | Gas | Plate Pretreatment | Normalised Absorption Change |
|---|---|---|---|
| 1 | $Cl_2$ | heated and pre-exposed to $C_6H_5Br$ | 0.53 |
| 2 | $Cl_2$ | heated and pre-exposed to $C_6H_5Cl$ | 0.51 |
| 3 | $Cl_2$ | none | 0.48 |
| 4 | $Cl_2$ | pre-exposed to $C_6H_5Br$ | 0.40 |
| 5 | $Cl_2$ | heated | 0.34 |
| 6 | $Cl_2$ | pre-exposed to $C_6H_5Cl$ | 0.34 |
| 7 | $C_6H_5Cl$ | none | 0.25 |
| 8 | $CHCl_3$ | none | 0.20 |
| 9 | $CH_2Cl_2$ | none | 0.20 |
| 10 | $C_6H_5Br$ | none | 0.19 |
| 11 | $CCl_4$ | none | 0.06 |
| 12 | $CHCl_3$ | heated | 0.02 |
| 13 | $CCl_4$ | heated | −0.04 |
| 14 | $CH_2Cl_2$ | heated | −0.06 |
| 15 | $C_6H_5Cl$ | heated | −0.09 |
| 16 | $C_6H_5Br$ | heated | −0.09 |
| 17 | $H_2S$ | none | −0.42 |

A coated plate as above can be used as a 'dipstick'. Dipped into, for example, chlorine or perchlorate in water, a typical bis-phthalocyanine will change from green to red, or into a reducing ion (e.g. sulphide) from green to blue, revealing information about the medium into which it was dipped.

Example 3

Detection Of Chlorine-Spectroscopic Measurement.

Chlorine experiments were carried out to test reproducibility of colour effects. Six non pre-heated plates prepared from heavy fraction rare earth bisphthalocyanine, prepared as described below, sublimed onto the back of an indium-tin-oxide-coated glass slide, provided with contact pads for resistive heating of the oxide if desired, were chosen from two batches, three having very intense green colouration and three less intense. All six plates were exposed to $Cl_2$ gas in excess. The spectra of the plates were recorded before and after exposure, then recorded again after being heated for 4 days at 140° C. The heating was to see the extent of recovery after such massive exposure.

Table 3 gives the results of intensity measurement around 670 nm (neutral green) before exposure and 500 nm (red oxidised) and 704 nm (red oxidised) after exposure. The results show that the measurement at 670 nm decreases while a new absorption peak appears at 704 nm and the absorption at 500 nm has increased considerably. Plates 1, 5 and 6 (the less intense plates) all show more of a small band at 605 nm than do plates 2, 3 and 4. It was previously observed that this band disappears on heat treating and this is associated with the low temperature phase. This shows that all the plates contain at least two phases, the ratio of which differs from one group to another depending, for example, on the sublimation history of the plate.

TABLE 3

| | BASE LINE CORRECTED ABSORPTIONS | | |
|---|---|---|---|
| PLATE NUMBER | ABSORPTION AT 670 nm = A | ABSORPTION AT 500 nm/A | ABSORPTION AT 704 nm/A |
| 2 | 2.24 | .39 | .41 |
| 4 | 1.65 | .25 | .25 |
| 3 | 1.49 | .24 | .25 |

TABLE 3-continued

BASE LINE CORRECTED ABSORPTIONS

| PLATE NUMBER | ABSORPTION AT 670 nm = A | ABSORPTION AT 500 nm/A | ABSORPTION AT 704 nm/A |
|---|---|---|---|
| 1 | .89 | .22 | .28 |
| 5 | .81 | .48 | .5 |
| 6 | .38 | .28 | .39 |

Normalised by zero absorption measurement.

The heavy fraction rare earth bis-phthalocyanines may be prepared as described in Preparative Example 1 below.

Example 4

Detection of chlorine using tetrabenzoazaporphyrin bis-macrocycles.

While the preceding examples relate to the use of a mixed rare earth bisphthalocyanine. It is also possible to employ novel bis-macrocycles wherein one or both macrocycles have a mono-, di-, or triazatetrabenzoporphyrin structure or a tetrabenzoporphyrin structure. This is exemplified as follows for two heavy fraction rare earth tetrabenzoazaporphyrin bis macrocycle mixtures in the detection of chlorine using uv/visible spectra recorded as described above and apparatus as described in FIG. 1. The tetrabenzoazaporphyrin mixtures, whose preparations are described below were coated onto a glass slide. The resulting spectra before and after exposure of chlorine are given in FIGS. 5 and 6, with the dotted line showing the spectrum before chlorine exposure and the full line showing the spectrum after exposure.

Figure 5:
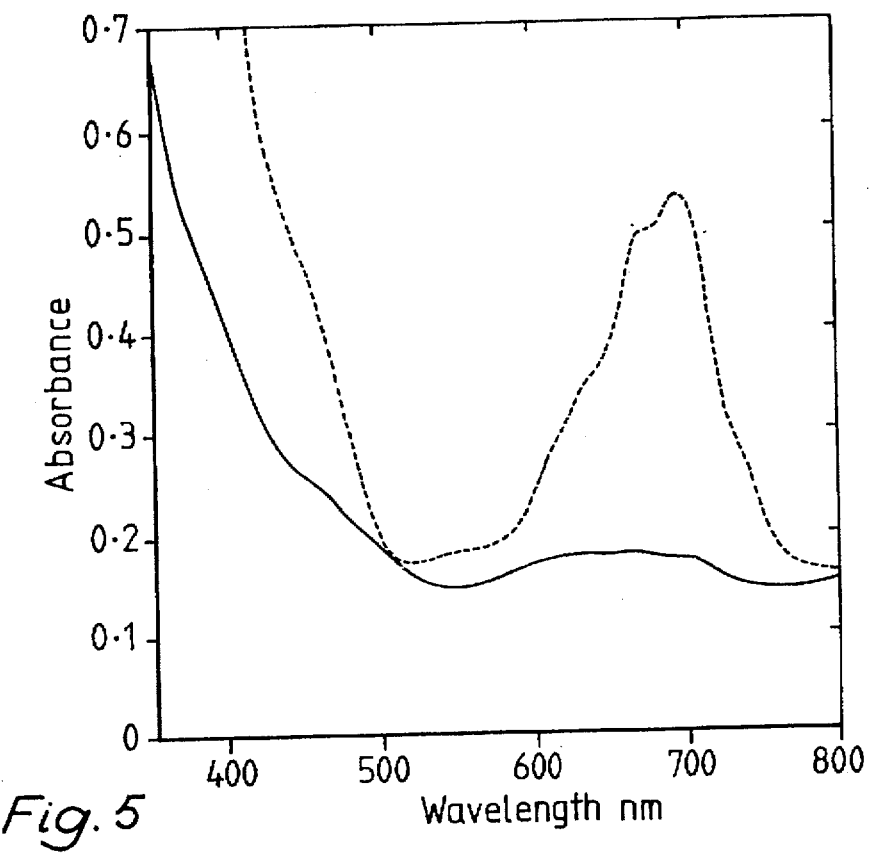
Figure 6:
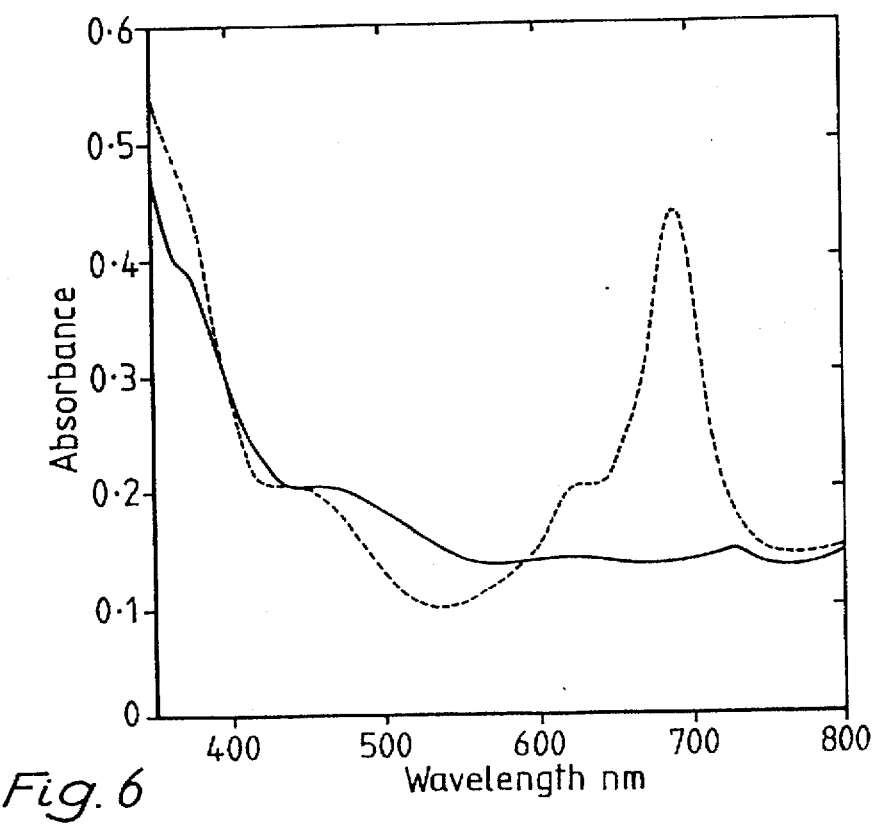

FIG. 5 shows the results for a heavy fraction rare earth tetrabenzoazaporphyrin mixture unsubstituted on the bridging carbon atom(s) and prepared generally as described in Preparative Example 2 below (Run No. 1) while FIG. 6 shows the results for a heavy fraction rare earth tetrabenzoazaporphyrin mixture substituted by ethyl on the bridging carbon atom(s) and prepared as described in Preparative Example 3 below.

Example 5

Detection of chlorine using ytterbium diphthalocyanine.

Additionally it is possible to substitute a single rare earth (or other metal) for the mixed rare earths used in the preceding examples. Ytterbium diphthalocyanine was obtained as described in Preparative Example 1 but substituting ytterbium acetate for the heavy fraction lanthanide acetate. 25 layers of ytterbium diphthalocyanine were deposited by Langmuir-Blodgett deposition onto an interdigitated gold electrode grid previously sublimed onto the non-conducting side of an indium-tin oxide-coated glass slide. Optical and electrical measurements were carried out as previously at a temperature of 113° C. for a) nitrogen only before exposure to chlorine gas and b) after 10 minutes exposure to 5 ppm chlorine gas in nitrogen.

Conductivity:

The current passed for a) was 117 µA

The current passed for b) was 16 µA

Figure 7:
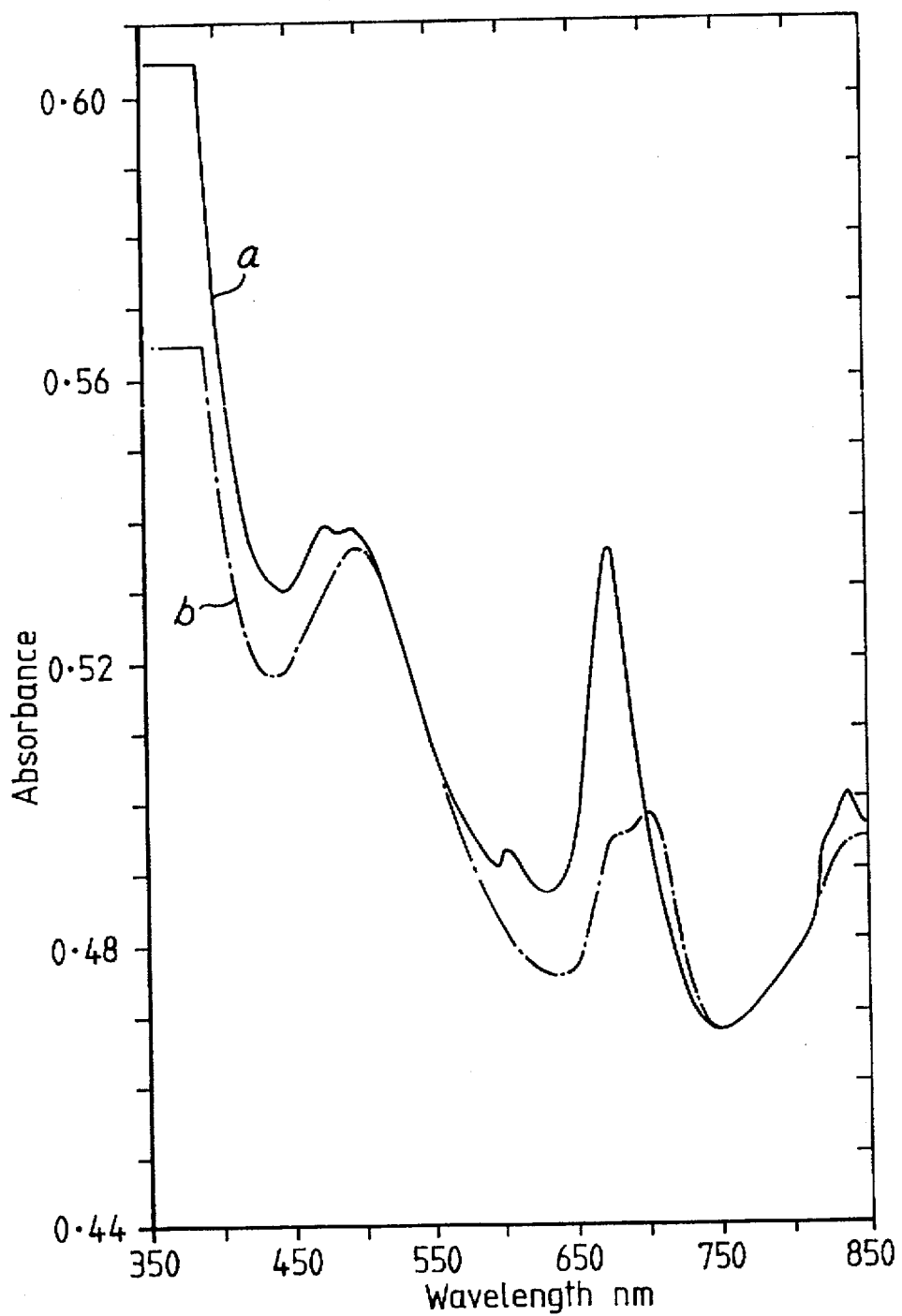

Optical measurements:

The uv/visible spectra (after base line correction) are given in FIG. 7, in which the dotted line shows the spectrum before chlorine exposure (a) and the full line shows the spectrum after exposure (b).

Preparative Example 1

Heavy fraction rare earth bis-phthalocyanine.

Dicyanobenzene and heavy-fraction lanthanide (rare-earth) acetate are mixed to give an 8:1 molar ratio of the former (=ligand) to metal. The mixture is then ground till intimately mixed and 2–4 g is placed in a 250 ml round-bottom flask, which is then loosely sealed with a silicone-greased stopper. The flask, supported in an upright position on a cork stand, is then placed in a 500 W rotating dish microwave oven and heated on a medium/high setting (300–400 W). After 20–30 minutes the reaction mixture forms a pale brown melt which turns dark green approximately 5 minutes later; the melt is left simmering for 45–60 minutes and then allowed to cool, whereupon it solidifies. The dark green solid formed is then ground into a fine powder, placed in a 3 inch diameter crystallising dish covered with a large (750 ml) beaker and heated in the microwave oven on a high setting (500 W) for 15 minutes. During the course of the heating most of the unreacted dicyanobenzene sublimes onto the beaker. The resulting green powder is then soxhlet extracted using diethyl ether for 4 hours to remove any remaining impurities: this step in the procedure is optional (and time consuming) but slightly improves (1–2%) the overall yield as less product is lost in subsequent sublimation steps if impurities are minimised at this stage. The remaining solid is then dried and purified by a series of high vacuum sublimations. In each case the material sublimed in the first few seconds is not collected as it is high in impurities (dicyanobenzene and higher polymers). The resulting material is a dark green crystalline powder (yield 10–15%).

Preparative Example 2

Heavy fraction rare earth tetrabenzoazaporphyrin mixture.

Methyl magnesium bromide (MeMgBr) (3M) was added to a constantly stirred mixture of phthalonitrile (PN) in diethyl ether, at room temperature, in the following molar ratios:

Run i) 1:1 PN/MeMgBr
ii) 2:1 PN/MeMgBr
iii) 4:1 PN/MeMgBr
iv) 8:1 PN/MeMgBr

It will be appreciated that methyl magnesium iodide or chloride may be substituted for methyl magnesium bromide.

Heavy fraction rare earth metal acetate, finely ground, was added.

It was noted that upon addition of the Grignard reagent, the PN quickly coagulated, and also the more Grignard added the browner the coagulate became.

The ether was allowed to evaporate off, and the solid was then placed in a furnace at 200° C. for half hr. The resulting dark mass was cooled and crushed. It was added to concentrated sulphuric acid, and then poured over ice. This was allowed to stand for several hours, and then filtered and air dried for 4–5 hours.

It was noticed that the material (i) prepared from 1:1 ratio is green while that from 4:1 is blue (i.e. more phthalocyanine-like in colour) and that the material (ii) is soluble in chloronapthalene and insoluble in dimethylformide.

These materials were found by HPLC (high pressure liquid chromatography) to be a mixture of the bis macrocycles in which the different compounds have distinguishable colour absorption peaks. The preparation was not such that pure bis-phthalocyanine or bis-tetrabenzoporphyrin could have been yielded.

The presence of a mixture of bis macrocycles was confirmed by investigation of the uv/visible spectra, in solution and as sublimed plates, and comparison with the different spectra obtained under the same conditions for the corresponding pure bis-phthalocyanine.

All the new mixtures were found to be electrochromic, giving new or improved colours such as brighter red.

Preparative Example 3

Ethyl substituted heavy fraction rare earth tetrabenzoazaporphyrin mixture.

10 g of phthalonitrile was suspended in 200 ml of dry diethyl ether. To this mixture 30 ml of 3M propyl magnesium iodide in ether was added with stirring. The colour of the mixture changed very rapidly from off white to deep purple. Stirring was continued and 4 g of heavy fraction acetate was added to the mixture when the phthalonitrile began to dissolved. After about 5 minutes a dark brown solid began to precipitate. The reaction was exothermic and some of the ether boiled off. After 2 hours the remaining ether was distilled off on a water bath. The resultant dark brown solid was heated to 300° C. The dropwise addition of water resulted in the evolution of white fumes followed by purple iodine vapour. When no further reaction occurred the solid was heated to 300° C. for another 30 minutes. On cooling the solid was washed with an ethanol/10% HCl mixture until the brown washings became colourless. Washing with hot distilled water/1% ammonia produced more brown washings and left a dark blue/green solid product.

HPLC analysis of the product gave evidence for the existence of five components which were believed to be predominantly tetra-, tri- and di-substituted rings. uv/visible spectra in solution and as sublimed plates confirmed the presence of a mixture of his macrocycles distinct from the corresponding bisphthalocyanine.

We claim:

1. A gas sensor comprising:
   optically transparent support means, supporting a solid state layer of a gas sensing component consisting of a metal bis-aromatic macrocycle or a mixture thereof wherein the two coordinating aromatic macrocycles are the same or different and are selected from the group consisting of bis-phthalocyanine analogs wherein of the total of the eight non-coordinating bridging nitrogen atoms of the two coordinating bis-phthalocyanine ligands, at least one has been replaced by carbon;
   optical absorption measuring means for measuring a change in optical absorption of said gas sensing component on exposure of said gas sensing component to an environment containing certain gases; and
   electrical conductivity measuring means for optionally measuring a change in electrical conductivity of said gas sensing component on exposure of said gas sensing component to an environment containing certain gases.

2. A gas sensor according to claim 1, wherein said gas sensing component is formed by deposition of a film or layer of said metal bis-aromatic macrocycle compound onto said optically transparent substrate.

3. A gas sensor according to claim 1, wherein the metal is a rare earth or a mixture of rare earths.

4. A gas sensor according to claim 1 and further comprising means for controlling the temperature of the optically transparent support means and the gas sensing component supported thereon.

5. A gas sensor according to claim 1, wherein said gas sensing component is selected from the group consisting of a metal bis-phthalocyanine, bis-tetrabenzoporphyrin or a bis-(mono, di or tri) azatetrabenzoporphyrin.

6. A gas sensor according to claim 5, wherein a heavy fraction mixture of rare earths is employed.

7. A gas sensor according to claim 5, wherein the heavy fraction mixture of rare earths is selected from two or more of the group consisting of dysprosium, holmium, erbium, thulium, ytterbium, lutetium and yttrium.

8. A gas sensor comprising:
   optically transparent support means, supporting a solid state layer of gas sensing component, said gas sensing component being selected from the group consisting of one or a mixture of rare earth bis-phthalocyanine analogs in which, of the total of eight non-coordinating bridging nitrogen atoms of the bis-phthalocyanines, at least one has been replaced by carbon and wherein the or each carbon is alkyl substituted;
   optical absorption measuring means for measuring a change in optical absorption of said gas sensing component on exposure of said gas sensing component to an environment containing certain gases; and
   electrical conductivity measuring means for optionally measuring a change in electrical conductivity of said gas sensing component on exposure of said gas sensing component to an environment containing certain gases.

9. A gas sensor according to claim 8, comprising: a transparent vessel;
   said transparent vessel having inlet means for independently introducing into said vessel sample and/or conditioning gas and outlet means for independently removing from said vessel sample and/or conditioning gas;
   a gas sensor element disposed inside said transparent vessel consisting of an optically transparent substrate supporting a metal bis-aromatic gas sensing component;
   optical absorption measuring means for measuring a change in optical absorption of said gas sensing component upon exposure of said gas sensing component to certain gases; and
   electrical conductivity measuring means for measuring a change in electrical conductivity of said gas sensing component upon exposure of said gas sensing component to certain gases.

10. A method of detecting or discriminating between gases, said method comprising the steps of:
    exposing to a gas a gas sensor comprising:
       optically transparent support means, supporting a solid state layer of a gas sensing component consisting of a metal bis-aromatic macrocycle or a mixture thereof wherein the two coordinating aromatic macrocycles are the same or different and are selected from the group consisting of bis-phthalocyanine analogs wherein of the total of the eight non-coordinating bridging nitrogen atoms of the two coordinating bis-phthalocyanine ligands, at least one has been replaced by carbon;
       optical absorption measuring means for measuring a change in optical absorption of said gas sensing component on exposure of said gas sensing component to an environment containing certain gases; and
       electrical conductivity measuring means for optionally measuring a change in electrical conductivity of said gas sensing component on exposure of said gas sensing component to an environment containing certain gases; and
    detecting a change in optical absorption and, optionally, electrical conductivity of the gas sensing component characteristic of the gas.

11. A method according to claim 10, wherein the gas is in solution.

12. A method according to claim 10, wherein the change detected is proportional to the concentration of gas.

13. A method according to claim 10, wherein the optically transparent support means and the gas sensing component supported thereon is preheated prior to exposure.

14. A method according to claim 10, and further comprising the steps of controlling the temperature of the optically transparent support means and the gas sensing component supported thereon.

15. A rare earth metal bis-aromatic macrocycle or mixtures thereof wherein the two coordinating aromatic macrocycles are the same or different and are selected from bis-phthalocyanine analogs wherein of the total of the eight non-coordinating bridging nitrogen atoms of the two coordinating bis-phthalocyanine ligands, at least one has been replaced by carbon, and wherein the or each carbon replacing the or each bridging nitrogen is alkyl substituted.

16. A rare earth bis-aromatic macrocycle or mixtures thereof according to claim 15, wherein the said metal is selected from the group consisting of dysprosium, holmium, erbium, thulium, ytterbium, lutetium, yttrium and mixtures thereof.

17. A rare earth bis-aromatic macrocycle or mixtures thereof according to claim 15, as a gas sensing component to detect and distinguish between gases.

18. A method for preparing a rare earth metal bis-aromatic compound or mixtures thereof according to claim 15, comprising the steps of adding a rare earth metal acetate or a mixture of rare earth metal acetates to a solution of a grignard agent and phthalonitrile and isolating the product.

19. A method according to claim 18, wherein the grignard reagent is a methyl magnesium halide.

20. A method according to claim 18, wherein the grignard reagent is a propyl magnesium halide.

* * * * *